United States Patent [19]

Kvanta et al.

[11] Patent Number: 5,093,121
[45] Date of Patent: Mar. 3, 1992

[54] METHOD FOR INCREASING THE PROTEIN CONTENTS OF MILK IN RUMINANTS

[75] Inventors: Endre Kvanta, Ängelholm; Mats Fischier, Båstad, both of Sweden

[73] Assignee: AB Medipharm, Angelholm, Sweden

[21] Appl. No.: 660,563

[22] Filed: Feb. 25, 1991

Related U.S. Application Data

[63] Continuation of Ser. No. 202,234, Jun. 3, 1989, abandoned.

[30] Foreign Application Priority Data

Jun. 11, 1987 [SE] Sweden ................................ 8702435

[51] Int. Cl.$^5$ ............................................. A61K 35/74
[52] U.S. Cl. ...................................... 424/93 H; 426/2
[58] Field of Search ............................... 424/93; 426/2

[56] References Cited

U.S. PATENT DOCUMENTS 3,956,482  5/1976  Hahn et al. ........................... 424/93

FOREIGN PATENT DOCUMENTS 7115643  4/1971  Japan ..................................... 424/93

*Primary Examiner*—Douglas W. Robinson
*Assistant Examiner*—Jean C. Witz

[57] ABSTRACT

The invention relates to a method of increasing the protein contents of milk in milk producing animals by introducing into the animal a culture of one or more non-pathogenic lactic acid producing live bacteria in admixture with a carrier. The invention also relates to a preparation containing said lactic acid producing bacteria in admixture with a carrier facilitating the optimal growth of the bacteria in the stomach-intestine system of the animal. The invention also deals with the use of non-pathogenic lactic acid producing live bacterial for increasing the protein contents of milk in milk producing animals.

8 Claims, No Drawings

METHOD FOR INCREASING THE PROTEIN CONTENTS OF MILK IN RUMINANTS

This is a continuation of copending application Ser. No. 07/202,234 filed on June 3, 1989 now abandoned.

FIELD OF THE INVENTION

BACKGROUND

Such animals are herein also called polystomachic animals or ruminants. In connection with breading of domestic animals, such as pigs, calves, broilers, horses, etc it is previously known that living or viable lactic acid producing bacteria in many cases can replace antibiotic substances in admixture with feed compositions. The purpose of using this principle is to stabilize the intestine channel of the animal by an antagonistic effect based on a conflict between lactic acid producing bacteria and pathogenic bacteria. This is previously known for example in SE-A-6913996-2 which discloses the use of a preparation containing living bacteria in connection with domestic animals. Such preparations are generally called probiotics. The predominant part of probiotics are bacteria belonging to lactic acid producing lactobacills or streptococcs. A small part belongs to the genus Bacillus, for example *Bacillus subtilis* or Leuconostoc. The majority of these are homofermentative lactic acid fermenters. Bacillus completely diverges from lactic acid bacteria both as to a species and function; members thereof are to a great extent used for enzym production, for example amylase and protease. Nevertheless Bacillus is used in the form of spores for the same purpose as lactobacills, i.e. to stabilize the intestine flora and thus increase the yield by an improved feed rate and an improved meat yield. Among commercial preparations based on the principle mentioned above, there are mentioned LBC, Lactiferm, Adjulac (lactic acid bacteria) and Toyocerin (spores of Bacillus).

By tradition probiotics are not administered to milk producing ruminants. The reason is that such animals are considered to be very stable as to their intestinal function. The intestinal micro flora of ruminants is further very complicated and those skilled in the art have the general opinion that it is not possible to affect the bacterial balance in the rumen by way of preparations containing bacteria added externally but are of the opinion that said balance is controlled by the composition of the feed as a primary factor. In certain cases efforts have been made to use probiotics even in ruminants, i.e. against mastitis. Reference is made to U.S. Pat. No. 4,591,499, which discloses a method of controlling mastitis in mammals comprising introducing into the mammary gland an amount of non-pathogenic lactic acid producing live bacteria. This treatment is based on the utilization of a bacterial antagonism between non-pathogenic lactic acid producing bacteria and pathogenic bacteria, e.g. coli bacteria, inhibiting the growth of the pathogenic bacteria. A possible way of supplying ruminants with lactic acid bacteria might be with the aid of a silage, i.e. green feed, which has been fermented with lactic acid bacteria. However, during storage of silage the lactic acid bacteria die. Thus, in silage there is no probiotic effect of naturally occuring or added so called ensilaging inoculants (such products are available on the market) consisting of living lactic acid bacteria.

SUMMARY OF THE INVENTION

The present invention is based on an effect of lactic acid producing bacteria belonging to the genera Lactobacillus, Pediococcus, Streptococcus and Leuconostoc, and of amylase and protease producing Bacillus, (preferably *B. subtilis* and *B. toyoi*), which effect resides in the fact that after administration of a culture of bacteria belonging to any of these genera or mixtures thereof, the composition of the milk is so affected that a significant daily increase of the protein content of the milk is obtained (a certain modest increase of the fat content of the milk is also noticed).

Expressed in another way, if a culture of living lactic acid producing bacteria is administered to healthy, milk producing ruminants the protein content of the milk produced is significantly increased. This surprising effect is not previously known and is completely unexpected to those skilled in the art.

The contents of the bacteria or mixtures thereof is not critical as long as the desired effect is obtained. However, a range of approximately $10^3-10^8$ CFU (colony forming unit) per animal per day has proved appropriate. The lower limit is of course dictated by the milk protein increasing effect and the upper limit is dictated by the desired absence of pathologic effects. Once the technical effect according to the invention has been established those skilled in the art are able to determine the content which is suitable in each case.

In carrying out the method of the present invention an effective quantity of one or more of the lactic acid producing bacteria is supplied to the milk producing animal. By "effective quantity" is meant a sufficient number of CFU to produce the desired increase of the protein content of the milk obtained from the milk producing animal. In supplying the lactic acid producing bacteria to the animal these are preferably present in a composition comprising a vehicle or a carrier, which is known per se, and which is so selected that it will promote the optimal growth of the bacteria in the stomach-intestine system of the animal. Such carrier is also used, which is quite conventional, to facilitate the supply of the bacteria in question. According to the invention there are two main categories of carriers or vehicles, i.e. those based on proteins and those based on carbohydrates. As non-limiting examples of protein based carriers there are mentioned milk powder and amino acids and as non-limiting examples of carbohydrate based carriers there are mentioned starch, cellulose and derivatives thereof, e.g. ethylhydroxyethylcellulose, carbohydroxymethylcellulose, etc., and sugars, such as glucose, fructose, dextrose, etc. The choice of carrier is not at all critical and is within the area of those skilled in the art. The bacteria or expressed more correctly, the culture of the bacteria is according to a preferred embodiment supplied to the milk producing animal in the form of a paste, a dry powder, in solution, preferably an aqueous solution, or in another suitable form, for example in the form of a feed composition. According to an embodiment of the invention, which is less preferred, mainly for practical and economical reasons, the culture of bacteria is administered directly into the rumen for example by way of a syringe. In this case the culture is injected admixed with a suitable carrier, for example in the form of an oil emulsion based on corn oil.

It can thus be seen that the composition of the preparation containing the culture of the lactic acid producing bacteria can be varied broadly and that in principle every combination of the culture and any carrier known per se can be used as long as the intended increase of the protein contents of the milk is produced. One skilled in the art can easily find the most appropriate combination. The administration method is of course also dependent on the type of animal and the age thereof.

There are various known strains of non-pathogenic lactic acid producing bacteria including the entire genera Lactobacillus, Streptococcus, Peciococcus, Leuconostoc and including some species of the genus Bacillus. Among the lactic acid producing species within these categories the following may be mentioned which have proved to be effective in performing the method of the present invention. They must not be regarded as limiting the invention. *Lactobacillus acidophilus, Lactobacillus bulgaricus, Lactobacillus casei, Lactobacillus cellobiosus, Lactobacillus confusus, Lactobacillus fermentum, Lactobacillus lactis, Lactobacillus leichmannii, Lactobacillus ruminis, Lactobacillus thermophilus, Streptococcus lactus, Streptococcus cremoris, Streptococcus thermophilus, Streptococcus faecium, Bacillus subtilis* and *Bacillus toyoi.*

There are of course a number of known sub-species of the foregoing species which can also be utilized. Those bacteria from the genus Streptococcus are generally preferred for use in the present invention and specifically *Streptococcus faecium.*

It has further been found that the culture of the bacteria in question or mixtures thereof in a most preferred embodiment is used in the form of a freeze-dried composition comprising conventional additives, such as cryoprotectant compounds, vitamins, trace elements and agents promoting free-flowing properties of the composition.

A characterizing feature of the bacteria providing a significant increase of milk protein is that they are isolated from other organisms than milk producing ruminants or are isolated from fresh green fodder or soil and that they are cultivated in vitro in such a way that a feasible amount of a mass of bacteria is obtained. As mentioned above, the mass of bacteria thus obtained is used either as such in appropriate doses or in admixture with other masses of bacteria, or is dried in an optional way and is supplied to the animal (orally) either in the form of a paste, a powder, a solution or mixed into feed.

DETAILED DESCRIPTION OF PREFERRED EMBODIMENTS

The effect of the bacteria providing an increase of the milk protein is illustrated by the following non-limiting examples. Cows were fed twice a day and each time they received 1 deciliter of a powdery preparation containing $10^8$ living freeze-dried bacteria either in a pure form belonging to one of the genera Lactobacillus, Pediococcus, Streptococcus, Leuconostoc or spores of Bacillus (subtilis or toyoi) or mixtures thereof, and further containing a carrier or a vehicle, the purpose of which being to support the growth of the bacteria in the rumen. The effect of the bacteria thus added is not observed until after about 4 days, the milk protein contents gradually increasing within a couple of days to a significantly higher level. On the other side, the effect of the bacteria decreases about 4 days after the supply has been finished.

Farm 1: Dairy cows were fed 8–10 kg (DM=dry mass) grass silage, 2 kg hay and a commercial grain-based concentrate mix according to milk yield. Feeding was twice daily and all feeds were offered simultaneously.

Farm 2: Dairy cows were fed 4–5 kg (DM) grass silage, 6 kg hay, 2 kg straw and a concentrate mix (grain and beet pulp) according to milk yield. Feeding was twice daily and all feeds were offered simultaneously.

Farm 3: Dairy cows were fed 2 kg (DM) grass silage, hay ad lib. and 8 kg commercial concentrate mix.

All herds were approximately 30 cows. All feeds were analyzed for DM and CP=Crude Protein. Roughages were analyzed for metabolizable energy content (ME). ME for the concentrates was taken from feeding tables. These values are presented in Table 1.

All farms were part of a herd control program run by the Swedish Insemination Association.

The cows were chosen based on an expected milk production of more than 25 kg milk per day. The cows on all farms were of the Swedish Red and White Breed which has a milk composition of approximately 3.5% protein and 4.0% fat.

Milk samples were taken 3 days a week, morning and evening, and analyzed on "Milco-scan 133" (infra-red scanning) for protein, fat and lactose.

TABLE 1

The contents of crude protein, CP (% of DM) and metabolizable energy, ME (MJ* kg $DM^{-1}$) in the feedstuffs on the different farms

| Feedstuff | Farm 1 | Farm 2 | Farm 3 |
|---|---|---|---|
| Concentrate | | | |
| CP | 12.7 | 13.1 | 14.9 |
| $ME^2$ | 12.6 | 9.8 | 12.8 |
| Silage | | | |
| CP | 18 | 21 | 19 |
| $ME^1$ | 10,1 | 9,2 | 8,9 |
| Hay | | | |
| CP | 9 | 10 | 10,9 |
| $ME^2$ | 9,7 | 8,9 | 9,2 |
| Straw | | | |
| CP | | 4 | |
| $ME^2$ | | 6.6 | |

Note 1. Analyzed according to the method described by Lindgren (1979)
Note 2 ME-values from tables in Eriksson et al. (1972)

STATISTICS

Only milk samples from the last week in each period were used and, as these observations are not independent, they were averaged. The data were analyzed using variation analyses (Anova, SAS, 1986) and GLM, to obtain least square means.

The model chosen was:

$$y = F\ S\ C\ (F \times S)\ T\ T \times F\ T \times S\ F \times S\ T\ (F \times S)$$

where;
F = farm
S = sequence (of treatment)
C = cow
T = treatment.

The most important dependent variable was assumed to be milk protein. Assuming an average of 3.5% milk protein, an expected increase of 0.1 units, coefficient of variation of 0.6 and 90% certainty for Type I and Type II errors, eight cows were needed on each farm to show differences both within and between farms. Fourteen cows were chosen as a safety margin. 90% certainty was chosen as this was primarily a pilot study. The low number of cows needed can be attributed to the small variation seen in milk protein content. Other parameters, such as fat, have higher variations and the statistical model was not chosen to show significant differences in these, even if FCM, milk fat and milk yield were analyzed as dependent variables.

RESULTS

The model chosen accounted for most of the variation as can be seen in Table 2, $R^2$. For the dependent variables milk yield, fat, protein and lactose contents, farms and cows are statistically highly significant. The only significant interaction was sequence × treatment. Treatment was statistically significant for milk protein and milk fat.

TABLE 2

Model fit (Anova) and least square means for the dependent variables in the statistical analysis. (Control = carrier substance only, Treatment = bacteria preparation, F = farm, C = cow and T = treatment.)

| Dependent variable | Independent variable | $R^2$ | CV | means control | treatment |
|---|---|---|---|---|---|
| Milk yield kg | F 11.60*** C 33.73*** T 2.51 | 0.98 | 5.11 | 24.21 | 23.78 |
| Protein kg | F 19.43*** C 10.95*** T 9.65*** | 0.96 | 0.77 | 0.82 | 0.86 |
| Lactose kg | F 12.10*** C 16.58*** T 0.08 | 0.97 | 7.33 | 1.49 | 1.44 |

\* $p < 0.05$
\*\* $p < 0.01$
\*\*\* $p < 0.001$

There was a large variation in the milk yield among cows whereby it is understandable that the cow variable was significant. It is assumed that the significant effects between farms are due mainly to differences in feeding, but this cannot be proven, and to differences between herds. The interaction, sequence × treatment is understandable as the trial lasted 10 weeks and lactation changes occurred.

The protein production is increased by 40 g per day when the cows received bacteria preparations, corresponding to $2 \times 10^8$ living bacteria daily.

The individual data on milk production for the three farms is presented in Table 3. These values are arithmetic means. Expressed as % of milk yield protein increases by approximately 0.25% units with the feeding of bacteria preparations.

order of 40 g per day per cow. All experiments showed significant results. Experiments similar to the above and carried out on other ruminants, such as goats and sheep, showed a significant increased daily milk protein production.

In summary it can thus be noted that the above examples show a completely new and unexpected effect, i.e. a significant increase of the milk protein of ruminants which is brought about by bacteria preparations supplied to the milk producing animal, preferably on a daily base. A daily increase of the protein contents of the milk amounting to about 40 g per cow or about 0.25% in the case of all ruminants, i.e. cows, sheep or goats, without a simultaneous increased feed consumption is of vital economical importance especially from a global point of view.

What is claimed is:

1. A method of increasing the protein content of the milk of milk producing ruminants, said method comprising introducing into a milk producing ruminant an effective quantity of a culture of a bacteria consisting of streptococcus faecium.

2. A method according to claim 1 wherein said introducing of the culture comprises orally introducing the culture to the milk producing ruminant as a paste, a dry powder, or a solution directly or in admixture with a feed.

3. A method according to claim 1, wherein the bacteria introduced into the ruminant has been cultured in a medium containing nutrients which ensure an optimal growth for said bacteria.

4. A method according to claim 1, wherein the bacteria is mixed with a carrier which facilitates the optimal growth of the bacteria in the stomach-intestine system of the ruminant.

5. A method according to claim 1 wherein said introducing of the culture comprises introducing said bacteria in a quantity of at least $10^3$ CFU per ruminant per day.

6. A method according to claim 5 wherein the bacteria is added in a quantity of $10^3$ to $10^8$ CFU per ruminant per day.

7. A method as claimed in claim 1 comprising obtaining said organism from fresh green fodder or soil.

8. A method as claimed in claim 7 wherein said in-

TABLE 3

Milk yield and composition with (treatment 2) and without (treatment 1) bacteria preparation as a feed additive. Arithmetic means ± standard deviations.

| | FARM 1 Treatment | | FARM 2 Treatment | | FARM 3 Treatment | |
|---|---|---|---|---|---|---|
| | 1 | 2 | 1 | 2 | 1 | 2 |
| Milk yield, kg/day | 24.71 ± 1.01 | 24.07 ± 1.01 | 19.57 ± 0.57 | 18.91 ± 0.66 | 28.21 ± 0.75 | 28.39 ± 0.71 |
| FCM, kg/day | 27.90 ± 0.95 | 22.93 ± 1.11 | 22.74 ± 0.78 | 20.53 ± 0.71 | 29.43 ± 0.71 | 26.65 ± 0.86 |
| Protein, % | 3.47 ± 0.06 | 3.71 ± 0.05 | 3.30 ± 0.04 | 3.63 ± 0.03 | 3.37 ± 0.05 | 3.5 ± 0.03 |
| Protein, kg/day | 0.85 ± 0.02 | 0.89 ± 0.02 | 0.64 ± 0.02 | 0.68 ± 0.03 | 0.95 ± 0.02 | 0.99 ± 0.02 |
| Lactose, % | 4.74 ± 0.09 | 4.78 ± 0.10 | 4.70 ± 0.03 | 4.80 ± 0.03 | 4.78 ± 0.03 | 4.85 ± 0.03 |
| Lactose, kg/day | 1.17 ± 0.05 | 1.15 ± 0.5 | 0.92 ± 0.03 | 0.91 ± 0.04 | 1.35 ± 0.04 | 1.37 ± 0.04 |

The experiments showed that the supply of bacteria preparations of the kind described above to high producing dairy cows provided a statistically significant increase of the milk protein contents which is on the creasing of the protein content of the milk is independent of fat content or quantity of the milk produced.

* * * * *